United States Patent
Kamee et al.

(10) Patent No.: US 11,304,591 B2
(45) Date of Patent: Apr. 19, 2022

(54) OPTICAL CONNECTION MODULE FOR ENDOSCOPE, ENDOSCOPE, AND ENDOSCOPE SYSTEM

(71) Applicant: OLYMPUS CORPORATION, Tokyo (JP)

(72) Inventors: Hiroyuki Kamee, Koganei (JP); Satoshi Ohara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/117,507

(22) Filed: Dec. 10, 2020

(65) Prior Publication Data

US 2021/0085160 A1 Mar. 25, 2021

Related U.S. Application Data

(63) Continuation of application No. PCT/JP2018/022213, filed on Jun. 11, 2018.

(51) Int. Cl.
*A61B 1/00* (2006.01)
*A61B 1/07* (2006.01)
*F21V 8/00* (2006.01)

(52) U.S. Cl.
CPC ...... *A61B 1/00126* (2013.01); *A61B 1/00195* (2013.01); *A61B 1/07* (2013.01); *G02B 6/0006* (2013.01)

(58) Field of Classification Search
CPC ..... A61B 1/07; A61B 1/00126; A61B 1/0019; G02B 6/0006; G02B 23/2469
See application file for complete search history.

(56) References Cited

U.S. PATENT DOCUMENTS

| | | | |
|---|---|---|---|
| 2009/0238521 A1 | 9/2009 | Oba | |
| 2011/0245616 A1* | 10/2011 | Kobayashi | A61B 1/0653 600/178 |
| 2013/0345517 A1* | 12/2013 | Morimoto | A61B 1/0661 600/178 |

(Continued)

FOREIGN PATENT DOCUMENTS

| | | |
|---|---|---|
| EP | 2 371 268 A1 | 10/2011 |
| EP | 2 702 928 A1 | 3/2014 |

(Continued)

OTHER PUBLICATIONS

International Search Report dated Sep. 11, 2018 received in PCT/JP2018/022213.

*Primary Examiner* — Leah Simone Macchiarolo
(74) *Attorney, Agent, or Firm* — Scully, Scott, Murphy & Presser, P.C.

(57) ABSTRACT

An optical connection module for an endoscope includes: an optical fiber having a fiber end surface and configured to guide a part of emitted light emitted from a light source and incident on the fiber end surface; a ferrule having a ferrule end surface with an opening of a through-hole into which the optical fiber is inserted, the ferrule including a scatterer configured to scatter, in an inside of the ferrule, a part of the emitted light incident on the ferrule end surface, the ferrule being configured to emit scattered light generated by scattering from a side surface; and an optical sensor arranged in the periphery of the side surface of the ferrule and configured to receive the scattered light.

16 Claims, 8 Drawing Sheets

(56) References Cited

U.S. PATENT DOCUMENTS

| | | | |
|---|---|---|---|
| 2014/0051987 A1* | 2/2014 | Kowshik | A61B 5/065 600/424 |
| 2014/0054450 A1* | 2/2014 | Shirota | G02B 23/26 250/226 |
| 2017/0255001 A1* | 9/2017 | Yamashita | A61B 1/0011 |
| 2018/0136454 A1* | 5/2018 | Yoshida | A61B 1/00112 |

FOREIGN PATENT DOCUMENTS

| | | |
|---|---|---|
| JP | 07-294329 A | 11/1995 |
| JP | 2009-223149 A | 10/2009 |
| JP | 2012-143414 A | 8/2012 |
| JP | 2014-000301 A | 1/2014 |
| JP | 2014-161639 A | 9/2014 |
| WO | 2010/070720 A1 | 6/2010 |
| WO | 2013/150897 A1 | 10/2013 |

* cited by examiner

OPTICAL CONNECTION MODULE FOR ENDOSCOPE, ENDOSCOPE, AND ENDOSCOPE SYSTEM

CROSS REFERENCE TO RELATED APPLICATION

This application is a continuation application of PCT/JP2018/022213 filed on Jun. 11, 2018, the entire contents of which are incorporated herein by this reference.

BACKGROUND OF THE INVENTION

1. Field of the Invention

The present invention relates to an optical connection module for an endoscope provided with an optical sensor, an endoscope including an optical connection module for an endoscope provided with an optical sensor, and an endoscope system including an optical connection module for an endoscope.

2. Description of the Related Art

The light source device for an endoscope is required to appropriately manage a light quantity of illumination light. In an endoscope system including a light source device using a xenon lamp as a light source, illumination light generated by the light source device is guided to the distal end portion via a bundle of a plurality of optical fibers (fiber bundle) that is inserted through a universal cord and an insertion portion. For example, the light quantity has been controlled by adjusting an optical aperture of the light source device on the basis of brightness of an endoscope image. That is, the light quantity of the xenon lamp is in a substantially stable state, and does not greatly change depending on a use condition.

On the other hand, a light source device for an endoscope using a light-emitting element such as a semiconductor laser diode (LD) or the like as a light source has been studied. The LD or the like generates heat at the time of driving, and the light quantity changes in accordance with the temperature of the element itself. Accordingly, the light quantity is detected in real time, and a driving signal to be supplied to the light source is controlled on the basis of the detection result. In order to detect the light quantity of the light source, a light-receiving element such as a photodiode or the like is used.

The illumination light of the endoscope has a larger light quantity than signal light used for data communication. Accordingly, when an arrangement position of the light-receiving element is different, the absolute value of the light quantity received by the light-receiving element is largely changed.

Japanese Patent Application Laid-Open Publication No. 7-294329 discloses an optical power monitor device that detects a light quantity of signal light guided by an optical fiber, by a photodiode disposed on a side surface of a ferrule made of glass into which the optical fiber is inserted. The signal light incident from a ferrule end surface is reflected by an inner circumferential surface of the ferrule and guided to a position where the photodiode is disposed.

That is, a lens has a numerical aperture equal to or greater than a numerical aperture of the optical fiber, a part of the signal light is condensed to the ferrule end surface in the periphery of an incident surface of the optical fiber. Furthermore, in order to reflect the signal light by the inner circumferential surface of the ferrule, an outer circumferential surface of the ferrule is covered by the reflection member.

SUMMARY OF THE INVENTION

An optical connection module for an endoscope according to an embodiment includes: an optical fiber having a fiber end surface and configured to guide a part of emitted light emitted from a light source and incident on the fiber end surface; a ferrule having a ferrule end surface with an opening of a through-hole into which the optical fiber is inserted, the ferrule including a scatterer configured to scatter, in an inside of the ferrule, a part of the emitted light incident on the ferrule end surface, the ferrule being configured to emit scattered light generated by scattering from a side surface; and an optical sensor arranged in a periphery of the side surface of the ferrule and configured to receive the scattered light.

An endoscope according to an embodiment has an optical connection module for an endoscope, the optical connection module for the endoscope includes: an optical fiber having a fiber end surface and configured to guide a part of emitted light emitted from a light source and incident on the fiber end surface; a ferrule having a ferrule end surface with an opening of a through-hole into which the optical fiber is inserted, the ferrule including a scatterer configured to scatter, in an inside of the ferrule, a part of the emitted light incident on the ferrule end surface, the ferrule being configured to emit scattered light generated by scattering from a side surface; and an optical sensor arranged in a periphery of the side surface of the ferrule and configured to receive the scattered light.

An endoscope system according to an embodiment has a light source device including an optical connection module for an endoscope, and an endoscope configured to emit illumination light guided by the light source device, the optical connection module for the endoscope includes: an optical fiber having a fiber end surface and configured to guide a part of emitted light emitted from a light source and incident on the fiber end surface; a ferrule having a ferrule end surface with an opening of a through-hole into which the optical fiber is inserted, the ferrule including a scatterer configured to scatter, in an inside of the ferrule, a part of the emitted light incident on the ferrule end surface, the ferrule being configured to emit scattered light generated by scattering from a side surface; and an optical sensor arranged in a periphery of the side surface of the ferrule and configured to receive the scattered light.

DETAILED DESCRIPTION OF THE PREFERRED EMBODIMENTS

First Embodiment

<Configuration of Endoscope>

Figure 1:
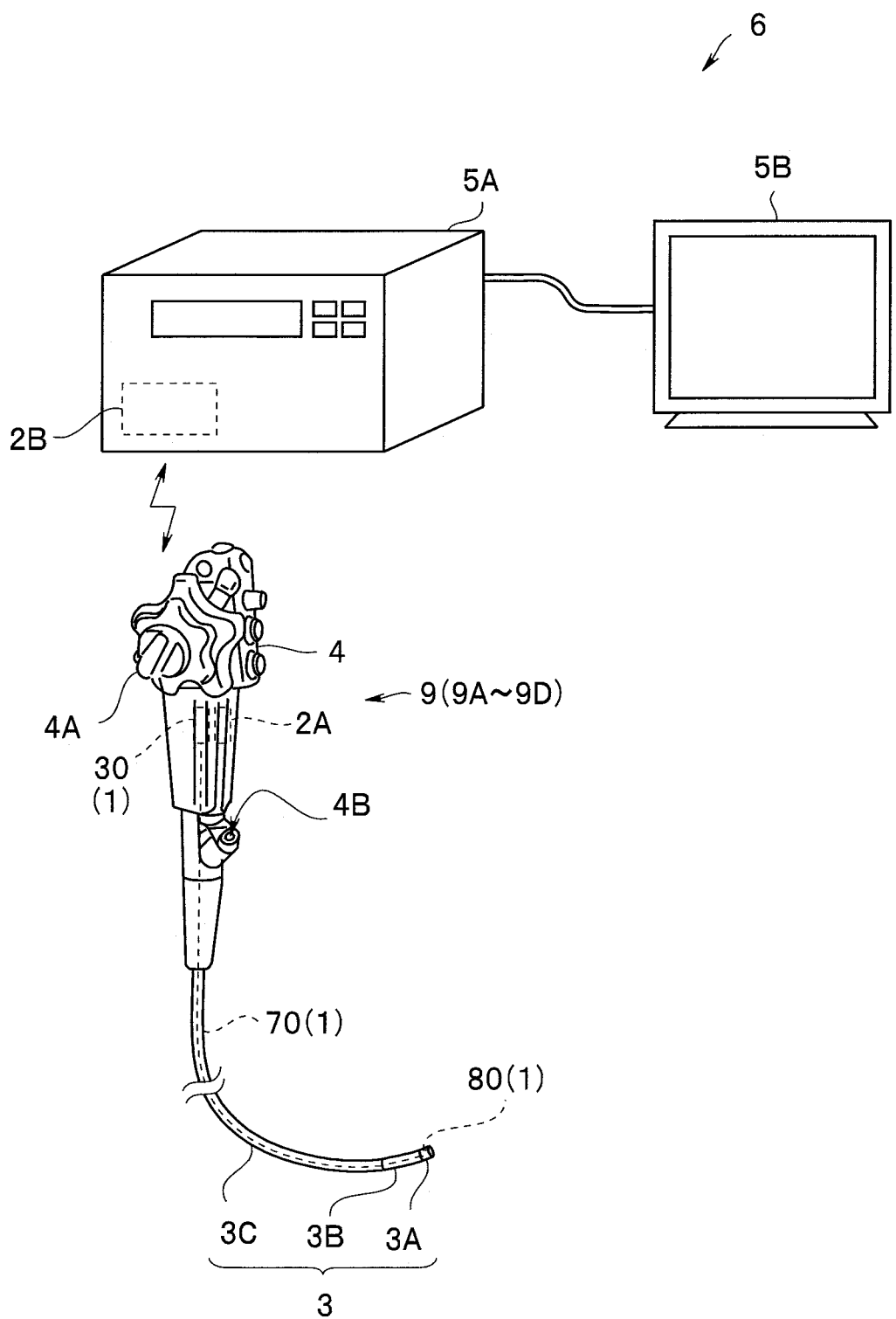
FIG. 1 is a perspective view of an endoscope system including an endoscope according to an embodiment.

As illustrated in FIG. 1, an endoscope system 6 including an endoscope 9 according to an embodiment is provided with the endoscope 9, a processor 5A, and a monitor 5B. The endoscope 9 has an insertion portion 3 and a grasping portion 4. The endoscope 9 is a so-called cordless endoscope. In the cordless endoscope, an image signal obtained by photographing an in-vivo image of a subject is wirelessly transmitted from a transmission unit 2A to a reception unit 2B of the processor 5A. The endoscope 9 incorporates a light source device 1 for an endoscope (hereinafter, referred to as a "light source device 1") including an optical connection module 30 for an endoscope of a pigtail type (hereinafter, referred to as an "optical connection module"), which will be described later in detail.

The cordless endoscope has better operability than an endoscope connected to the processor and the light source device by a universal cord.

The insertion portion 3 includes a distal end portion 3A, a bendable bending portion 3B provided continuously to a proximal end portion of the distal end portion 3A, and an elongated flexible portion 3C provided continuously to a proximal end portion of the bending portion 3B. The bending portion 3B is bent by an operation of an angle knob 4A, which rotates, of the grasping portion 4. The grasping portion 4 has a channel opening 4B of a treatment instrument channel which is inserted through the insertion portion 3.

On the distal end portion 3A of the endoscope 9, although not illustrated in the drawings, an illumination optical system that emits illumination light is disposed.

Figure 2:
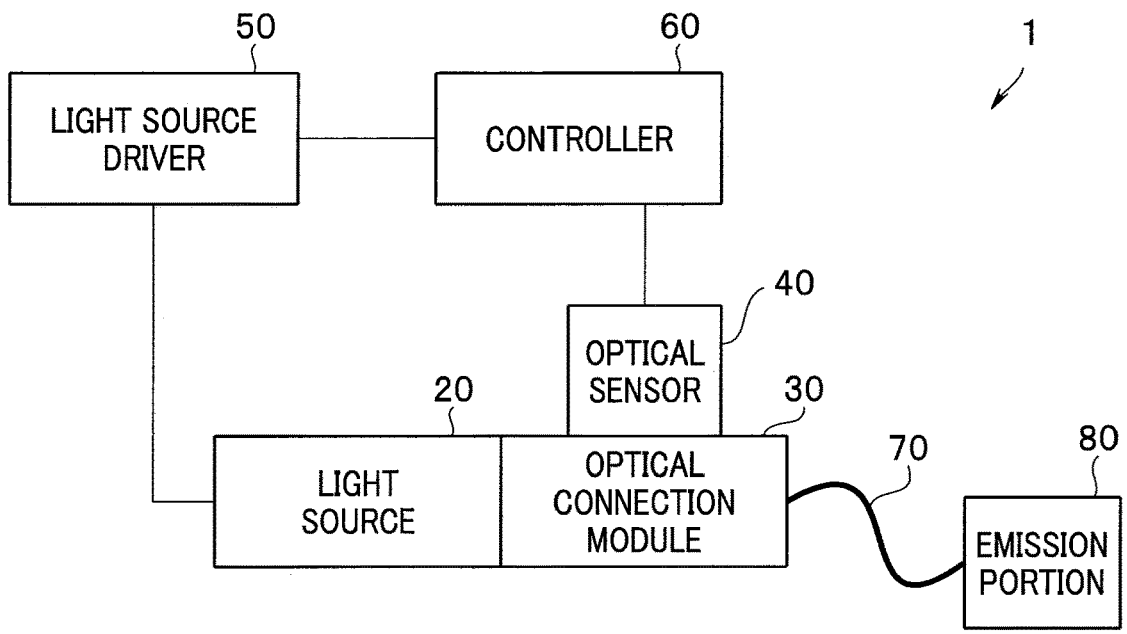
FIG. 2 is a configuration diagram of a light source device including an optical connection module for an endoscope according to a first embodiment.
Figure 3:
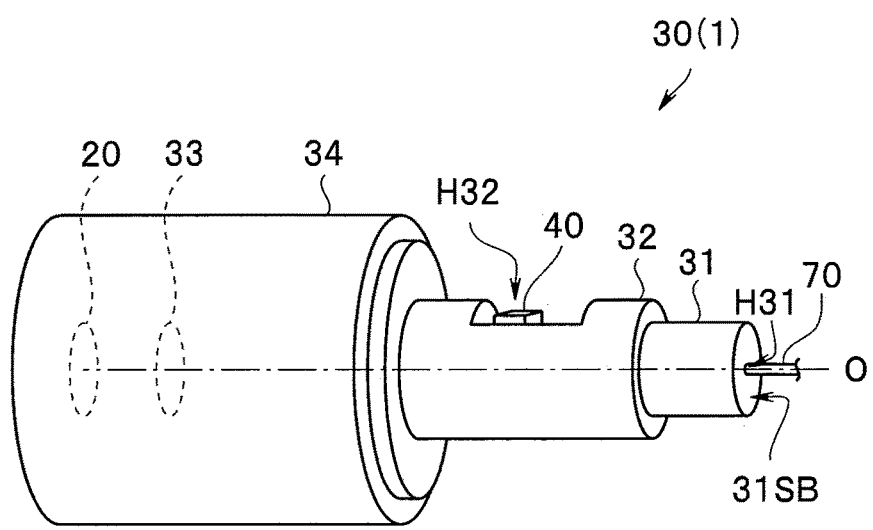
FIG. 3 is a perspective view of the light source device including the optical connection module for the endoscope according to the first embodiment.
Figure 4:
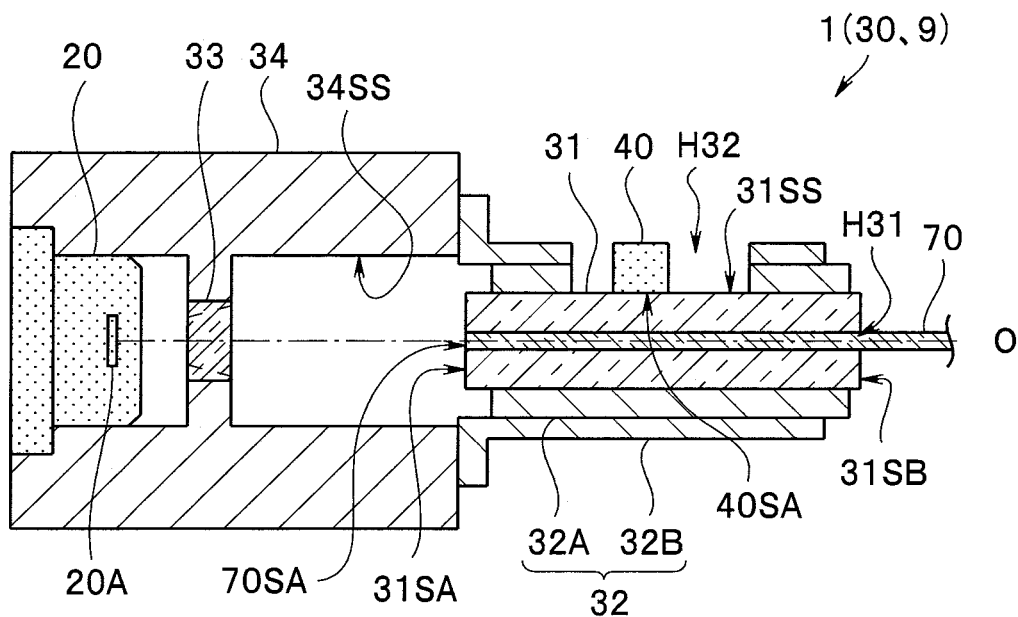
FIG. 4 is a cross-sectional view of the light source device including the optical connection module for the endoscope according to the first embodiment.
Figure 5:
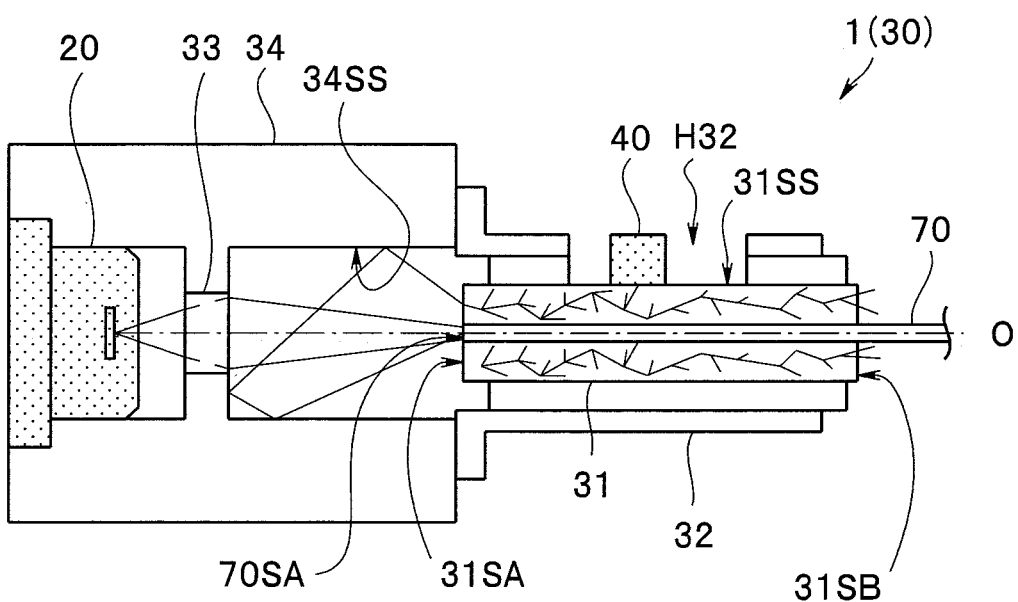
FIG. 5 is a schematic diagram for illustrating an optical path in the light source device including the optical connection module for the endoscope according to the first embodiment.

In the light source device 1, main portions such as the optical connection module 30 and the like are disposed in the grasping portion 4, and the illumination light is guided to an emission portion 80 at the distal end portion 3A by passing through one optical fiber 70 that is inserted through the insertion portion 3, and is emitted from the illumination optical system (see FIG. 2). The light source device 1 that guides the illumination light using only the one optical fiber 70 has the insertion portion 3 having a small diameter, and is therefore low invasive.

Note that although the endoscope 9 is a flexible endoscope for medical use, an endoscope according to another embodiment may be a rigid endoscope, or may be an endoscope for industrial use. Furthermore, an endoscope according to another embodiment may be an endoscope connected to the processor by a universal cord.

<Configuration of Light Source Device for Endoscope>

As illustrated in FIG. 2 to FIG. 5, the light source device 1 is provided with, as a main constituent element, the optical connection module (optical connection structure) 30 according to the embodiment including a ferrule 31, an optical sensor 40, and the optical fiber 70.

In the following description, it should be noted that the drawings based on each embodiment are schematic, and a relationship between the thickness and the width of each portion, a thicknesses ratio and a relative angle of the portions, and the like differ from actual ones. Among the drawings, portions, which differ in the mutual dimensional relationship and ratio, are included in some cases. Furthermore, illustration of constituent elements and reference numerals given thereto are partially omitted in some cases. For example, a conducting wire of the optical sensor 40 is not illustrated.

In the optical connection module 30, a part of emitted light (illumination light) emitted from the light source 20 is guided to the emission portion 80 through the optical fiber 70 which is a light guiding member.

For example, on the emission portion 80, a phosphor that generates yellow light when receiving blue light emitted from a light emitting portion 20A of the light source 20 is disposed. Accordingly, from the emission portion 80, white light including the blue light and the yellow light is emitted as illumination light. The light source device 1 may be provided with the light source 20 that emits white light.

The light source device 1 is further provided with a controller 60 that adjusts a light quantity of the emitted light by controlling the light source 20 in accordance with an output value of the optical sensor 40. That is, by the control of the controller 60, a driving signal outputted from a driver 50 to the light source 20 is adjusted.

Note that the controller 60 and the light source driver 50 may be separate bodies from the optical connection module 30. For example, the controller 60 may be disposed in the processor 5A of the endoscope 9. Furthermore, the CPU of the processor 5A of the endoscope 9 may have the function of the controller 60.

The light source 20 is of a CAN type in which a small semiconductor light-emitting element of a semiconductor laser diode (LD) or a light-emitting diode (LED) is housed in a package.

A part of the emitted light (illumination light) emitted from the light source 20 is incident on a fiber end surface 70SA of the optical fiber 70 by the optical connection module 30, and is guided. That is, the optical fiber 70 has the fiber end surface 70SA, and guides the part of the emitted light which is emitted from the light source 20 and incident on the fiber end surface 70SA.

The circular column-shaped ferrule 31 has an opening of a through-hole H31 into which the optical fiber 70 is inserted, on a ferrule end surface 31SA. The inner diameter of the through-hole 1131 is slightly larger than the outer diameter of the optical fiber 70, and an adhesive (not illustrated) is disposed between the outer circumferential surface of the optical fiber 70 and the inner surface of the through-hole H31.

The optical connection module 30 is further provided with a lens 33 and a holder 34. The lens 33 condenses the emitted light emitted from the light source 20 onto the fiber end surface 70SA. The holder 34 is a holding member to which the light source 20, the lens 33, and the ferrule 31 are fixed. The holder 34 manufactured by processing of a metal such as stainless steel, brass, or the like has an inner surface 34SS that configures a space including an optical path of the emitted light condensed by the lens 33.

Additionally, a numerical aperture (NA) of the lens 33 is equal to or less than a numerical aperture (NA) of the optical fiber 70. That is, when the emitted light condensed by the lens 33 is incident on the fiber end surface 70SA (strictly speaking, a core end surface of the optical fiber 70 formed of a core and a clad), the emitted light is wave-guided inside the core with high efficiency, and is not emitted to the outside through the clad.

In general, in a light source device that transmits an optical signal, since the optical signal deteriorates due to multiple reflection, the fiber end surface is tilted relative to a plane perpendicular to the optical axis of the optical fiber. However, in the light source device 1 that transmits the illumination light, the fiber end surface 70SA is polished perpendicularly to an optical axis O of the optical fiber 70. Accordingly, most of the emitted light is incident on the optical fiber 70, and thus transmission efficiency is high. Even when the emitted light is incident perpendicularly on the fiber end surface 70SA, a part of the emitted light is reflected by the fiber end surface 70SA. Note that the optical axis O of the optical fiber 70 coincides with the principal axis through which the strongest light in a light flux of the emitted light condensed by the lens 33 passes.

In the light source device 1, the emitted light reflected by the fiber end surface 70SA is further reflected by the inner surface 34SS of the holder 34, and is incident on the ferrule end surface 31SA. The emitted light may be reflected by the surface of the lens 33, or may be reflected a plurality of times by the inner surface 34SS.

The ferrule 31 includes a scatterer that scatters a part of the emitted light incident on the ferrule end surface 31SA in the inside of the ferrule 31, and emits the scattered light generated by scattering from a side surface 31SS which is the outer circumferential surface. The emitted light incident on the ferrule end surface 31SA is a part of the emitted light (emitted light to be scattered) that is different from the part of emitted light (emitted light to be guided) incident on the fiber end surface 70SA.

Since the ferrule 31 scatters light in the inside thereof, a reflection member covering the ferrule for reflection on the outer surface of the ferrule is not required.

The ferrule 31 is fixed in a state of being inserted into a sleeve 32 which is a holding member, and is thus fixed to the holder 34 as a result. As will be described later, in order to highly accurately position and then fix the ferrule 31 (optical fiber 70) to the holder 34, the sleeve 32 has a first cylindrical body 32A and a second cylindrical body 32B. The ferrule 31 is inserted into and fixed to the first cylindrical body 32A. The first cylindrical body 32A is inserted into and fixed to the second cylindrical body 32B. Additionally, the second cylindrical body 32B is fixed to the holder 34.

The optical sensor 40 is arranged in a sleeve opening H32 of the sleeve 32, that is, in the periphery of the side surface 31SS of the ferrule 31, in a state in which a light receiving surface 40SA is parallel to the optical axis O of the optical fiber 70. In order to perform positioning of the optical sensor 40 to a position with an appropriate light quantity, the sleeve opening H32 is preferably a groove having an elongated shape in the optical axis direction such that a plurality of optical sensors 40 can be arranged, for example. The sleeve opening H32 may be a slit provided so as to extend to a rear portion of the sleeve 32.

The optical sensor 40 including a light-receiving element such as a photodiode (PD) or the like receives the scattered light emitted to the side surface 31SS of the ferrule 31, and outputs a detection signal of an output value corresponding to the light quantity of the scattered light. The optical sensor 40 may perform primary processing on the detection signal outputted by the light-receiving element, and then output the processed signal.

In the ferrule 31, for example, a light quantity of the scattered light emitted from a rear end surface 31SB on the opposite side of the ferrule end surface 31SA is preferably greater than 0.1% and less than 80% of the light quantity of blue emitted light (wavelength: 450 nm) incident perpendicularly on the ferrule end surface 31SA, and particularly preferably greater than 5% and less than 60% of the light quantity of the blue emitted light.

In the case where the light quantity is greater than the lower limit of the above-described range, a detection signal of an appropriate output value is outputted from the optical sensor 40. In the case where the light quantity is less than the upper limit of the above-described range, since the light quantity dependence of the scattered light on an arrangement position of the optical sensor 40 is small, the output value of the detection signal from the optical sensor 40 does not largely change depending on the arrangement position.

The light source device 1 including the optical connection module 30 can accurately detect the light quantity because the optical sensor 40 receives the scattered light having an appropriate light quantity. Accordingly, the light source device 1 can emit illumination light having an appropriate light quantity. The endoscope 9 having the light source device 1 including the optical connection module 30 can obtain an endoscope image with appropriate brightness by the illumination light having the appropriate light quantity.

Note that the light source device 1 is incorporated in the endoscope 9. However, the light source device may be a separate body from the endoscope, or may be attachable/detachable to/from the endoscope. For example, the light source device is used by being inserted into the treatment instrument channel from the channel opening 4B. For example, the light source device is inserted into the treatment instrument channel of an endoscope that performs white light illumination, and radiates narrow-band illumination light. Furthermore, the light source device radiates, for example, a cauterization laser beam for the treatment, instead of the illumination light.

Furthermore, the emitted light from the light source 20 may be guided by, for example, the optical fiber, and be incident on the optical connection module 30.

<Manufacturing Method for Light Source Device>

Figure 6:
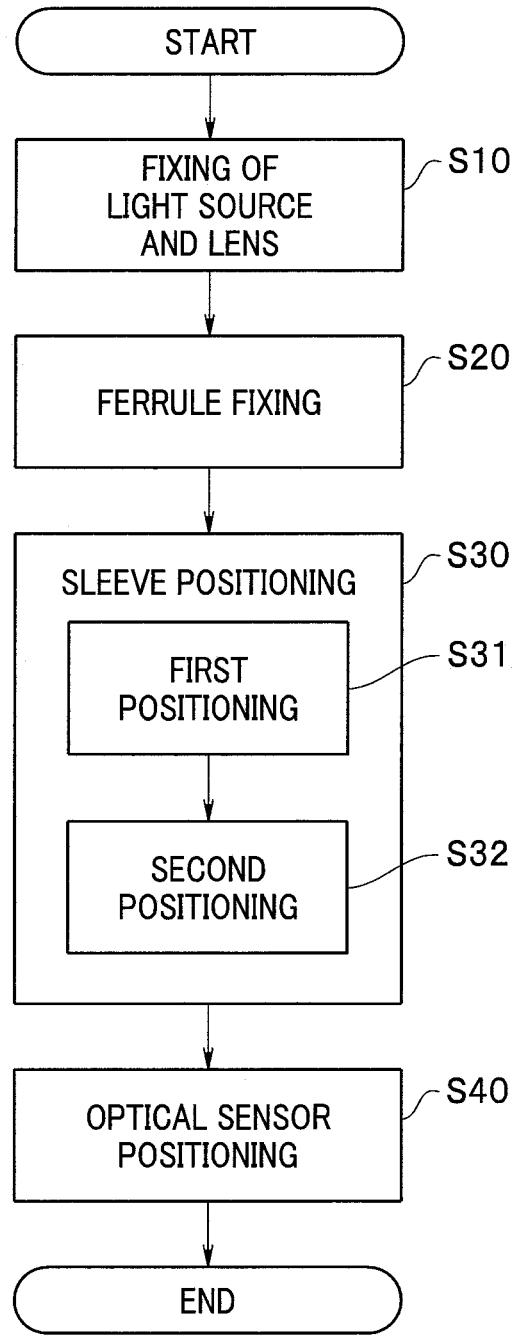
FIG. 6 is a flowchart of a manufacturing method of the light source device including the optical connection module for the endoscope according to the first embodiment.

Next, along a flowchart in FIG. 6, a manufacturing method of the light source device 1 including the optical connection module 30 will be briefly described.

<Step S10> Light Source and Lens Fixing Process

The light source 20, which is the CAN-type light-emitting element (LD), and the lens 33 are highly accurately positioned and fixed to the holder 34.

The light source 20 may be of a so-called bare chip type. Furthermore, an end portion of a waveguide that emits illumination light guided from a light source which is a separate body through the waveguide may be used as the light source 20. That is, the light source 20 is not limited to a self-luminous light-emitting element or the like. Furthermore, the optical connection module 30 may be fixed to a light source module including the light source 20, the lens 33, and the holder 34.

The lens 33 may be a single lens, or a lens group including a plurality of lenses, as long as the lens has a predetermined numerical aperture.

On the inner surface 34SS of the holder 34 manufactured by processing of a metal such as stainless steel, brass, or the like, a reflectance of light having the wavelength of the emitted light is preferably equal to or greater than 30%, and particularly preferably equal to or greater than 50%. In order to increase the reflectance, the inner surface 34SS may be polished and formed in a mirror surface, or whitish paint having a high reflectance may be applied on the inner surface 34SS. The reflectance is a ratio of the light that is not absorbed/transmitted into/through the inner surface 34SS and is reflected thereby, of the emitted light incident perpendicularly on the inner surface 34SS.

<Step S20> Ferrule Fixing Process

The ferrule 31 to which the optical fiber 70 is fixed is inserted into the first cylindrical body 32A of the sleeve 32, and is fixed by an adhesive or the like (not illustrated). Note that the ferrule end surface 31SA and the fiber end surface 70SA are polished perpendicularly to the optical axis O of the optical fiber 70 after the optical fiber 70 is inserted into and fixed to the ferrule 31.

The light quantity of the scattered light emitted from the rear end surface 31SB of the ferrule 31 varies depending on the length of the ferrule 31 in the optical axis direction. However, the length of the ferrule 31 is defined, by a specification, for example, as 1 cm. Accordingly, in order to make the light quantity of the scattered light of the ferrule 31 fall within the above-described range, selection of the material of the ferrule 31 is important.

The scatterer of the ferrule 31 is preferably formed by a material that transmits and scatters light, a mixed material of a plurality of materials that transmits light and has different refractive indexes, or a polycrystalline material that transmits light. The material of the ferrule 31 may be a white resin or glass in which filler such as particles or the like are dispersed, but in particular, a ceramic is preferable.

The optical fiber 70 may be made of either glass or resin, or may be either a multi-mode fiber or a single-mode fiber, as long as the illumination light can be guided to the emission portion 80. In addition, in the case where the optical fiber 70 is a multi-mode fiber, either a step index or a graded index may be used.

Note that the order of step S10 and step S20 may be reversed.

By the first cylindrical body 32A to which the ferrule 31 is fixed being inserted into the second cylindrical body 32B of the sleeve 32, the first cylindrical body 32A is inserted into the second cylindrical body 32B.

Note that the front portion (an end portion closer to the light source 20) of the second cylindrical body 32B is formed in a donut-shaped flat plate that makes contact with the rear surface of the holder 34.

<Step S30> Sleeve Positioning Process

In order to perform positioning of a fixing position of the sleeve 32 (the first cylindrical body 32A and the second cylindrical body 32B) to the holder 34, a driving signal having a predetermined intensity is supplied to the light source 20, and the emitted light is condensed in the vicinity of the fiber end surface 70SA by the lens 33. Subsequently, the positioning of the sleeve 32 is performed while monitoring the light quantity of the illumination light emitted from the emission portion 80 of the optical fiber 70 by, for example, a light quantity meter.

For the positioning, the holder 34, the first cylindrical body 32A, and the second cylindrical body 32B are grasped by a jig capable of finely adjusting relative positions.

The positioning process of the sleeve 32 with respect to the holder 34 includes a first positioning process (step S31) for determining a first position in an in-plane direction orthogonal to the optical axis, and a second positioning process (step S32) for determining a second position in the optical axis direction.

In the first positioning process (S31), while moving the second cylindrical body 32B in the two in-plane directions orthogonal to the optical axis O in a state in which the front surface of the second cylindrical body 32B is in contact with the rear surface of the holder 34, a position where the light quantity of the illumination light is maximized is determined. Subsequently, the second cylindrical body 32B is welded at a plurality of locations to the holder 34 using, for example, a YAG laser.

In the second positioning process (S32), while moving the position of the first cylindrical body 32A inserted into the second cylindrical body 32B in the optical axis direction, a position where the light quantity of the illumination light is maximized is determined. Subsequently, the first cylindrical body 32A is welded at a plurality of locations to the second cylindrical body 32B using, for example, a YAG laser.

<Step S40> Optical Sensor Positioning Process

The optical sensor 40 is arranged in the sleeve opening H32 of the sleeve 32, and the intensity of a detection signal (photocurrent) outputted by the optical sensor 40 is monitored. In the optical sensor positioning process (S40), while moving the position of the optical sensor 40 in the optical axis direction in the sleeve opening H32, the position where the optical sensor 40 outputs the optimum output signal is determined.

The position of the optimum output signal of the optical sensor 40 is a position where an output signal corresponding to the light quantity is outputted, and on which the scattered light having the light quantity in the dynamic range of the optical sensor 40 is incident, and is preferably a position on which the scattered light having the light quantity at the center of the dynamic range is incident. Then, the optical sensor 40 is fixed to the sleeve 32 by, for example, an adhesive (not illustrated).

Note that a plurality of sleeve openings may be provided in a direction parallel to the optical axis O of the sleeve 32, and the optical sensor 40 may be arranged in any optimum sleeve opening among the plurality of sleeve openings. In the case were there is the plurality of sleeve openings, the length of the sleeve opening in the optical axis direction may be substantially the same as the length of the optical sensor 40. In addition, the second cylindrical body 32B may include one sleeve opening formed of a groove or a slit, and the first cylindrical body 32A may include a plurality of sleeve openings.

Furthermore, in the case where it is expected that the light quantity of the light source 20 largely changes, a plurality of optical sensors 40 may be arranged in one sleeve opening of the sleeve 32, or the optical sensors 40 may be respectively arranged in a plurality of sleeve openings of the sleeve 32. In the light source device having the plurality of optical sensors 40, in accordance with the output value of the optical sensor 40 arranged at the optimum position in accordance with a change in the light quantity, the light quantity of the emitted light emitted from the light source 20 can be controlled.

Modification of First Embodiment

Light source devices 1A to 1C and endoscopes 9A to 9C each including an optical connection module according to each modification of the first embodiment are similar to the light source device 1 and the endoscope 9 including the optical connection module according to the first embodiment and have the same effects as those thereof, and therefore, constituent elements having the same functions are given the same reference numerals, and the description thereof will be omitted.

First Modification of First Embodiment

Figure 7:
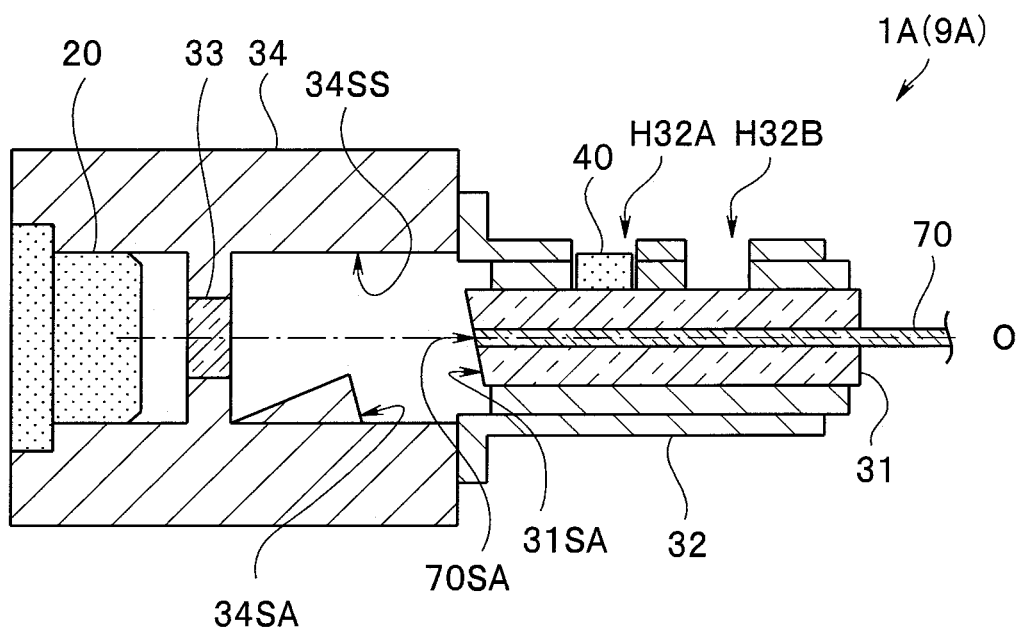
FIG. 7 is a cross-sectional view of a light source device including an optical connection module for an endoscope according to a first modification of the first embodiment.

As illustrated in FIG. 7, in the light source device 1A including the optical connection module according to the present modification, the fiber end surface 70SA is tilted relative to a plane perpendicular to the optical axis O of the optical fiber 70. Accordingly, the light source device 1A has lower incidence efficiency than that of the light source device 1, but more emitted light is reflected by the fiber end surface 70SA.

Furthermore, the inner surface 34S S of the holder 34 has a tilted surface 34SA facing the ferrule end surface 31SA. The tilt angle of the fiber end surface 70SA and the tilt angle of the tilted surface 34SA are set in a state in which the emitted light reflected by the fiber end surface 70SA is incident on the tilted surface 34SA, and second reflected light reflected by the tilted surface 34SA is incident on the ferrule end surface 31SA.

In the light source device 1A, more scattered light is received by the optical sensor 40 than in the light source device 1. The light source device 1A can accurately detect the light quantity because the optical sensor 40 receives the scattered light having an appropriate light quantity. Accordingly, the light source device 1A can emit illumination light having an appropriate light quantity.

Note that the light source device 1A has two sleeve openings H32A and H32B in the direction parallel to the optical axis O of the sleeve 32, and the optical sensor 40 is arranged in the sleeve opening H32A in which the light quantity of the scattered light is optimum, of the sleeve openings H32A and H32B. Note that it goes without saying that the sleeve 32 may have three or more sleeve openings.

Second Modification of First Embodiment

Figure 8:
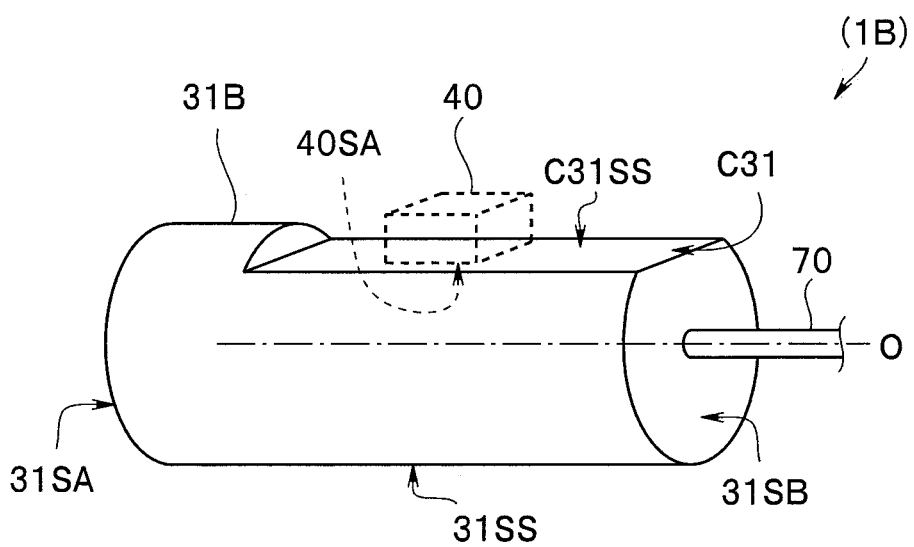
FIG. 8 is a perspective view of a ferrule of a light source device including an optical connection module for an endoscope according to a second modification of the first embodiment.

As illustrated in FIG. 8, a ferrule 31B of the light source device 1B including the optical connection module according to the present modification has a substantially circular column shape, and has a planar cutout region C31SS formed by a cutout C31 (D-cut) on the side surface (outer circumferential surface) 31SS. The optical sensor 40 is arranged in a state in which the light receiving surface 40SA faces the cutout region C31SS.

More scattered light is emitted from the cutout region C31SS than that from the side surface 31SS without the cutout C31. The light source device 1B can accurately detect the light quantity because the optical sensor 40 receives the scattered light having an appropriate light quantity. Accordingly, the light source device 1B can emit illumination light having an appropriate light quantity.

Note that in the case where the optical sensor 40 is housed in a hemispherical transparent cover member, a cutout having a semicircular cross section may be formed in conformity with the shape of the optical sensor 40.

Furthermore, the planar region C31SS is not limited to a region formed by the D-cut cutout C31. For example, on a part of the side surface 31SS of the ferrule, a recessed portion in which the planar region C31SS serves as a bottom surface may be formed.

Figure 9:
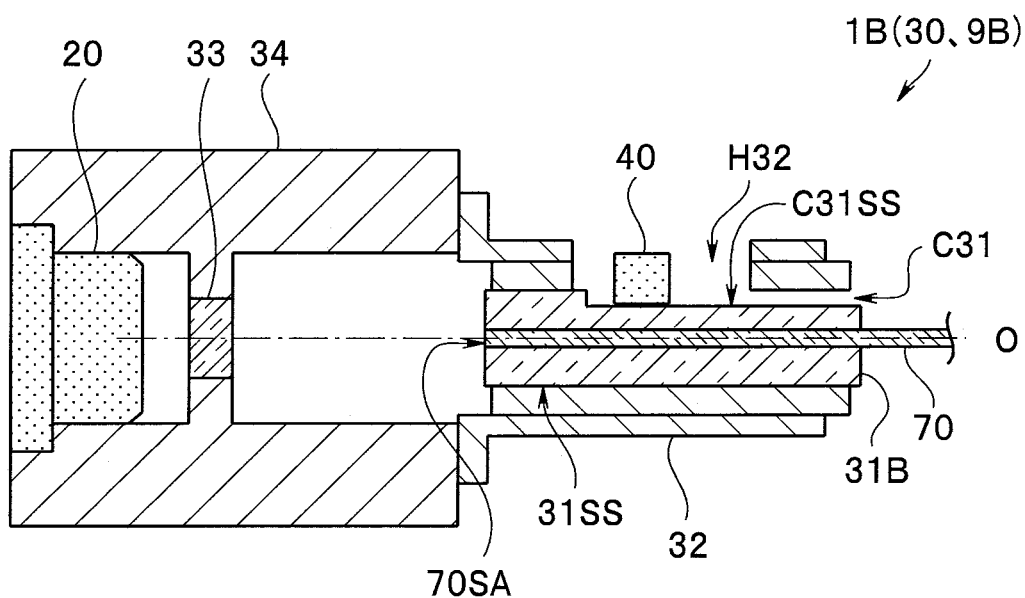
FIG. 9 is a cross-sectional view of the light source device including the optical connection module for the endoscope according to the second modification of the first embodiment.

Note that as illustrated in FIG. 9, the cutout C31 (cutout region C31SS) is not formed up to the ferrule end surface 31SA. Accordingly, a region of the side surface 31SS of the ferrule 31B, which is closer to the light source 20 than the cutout C31 (cutout region C31SS), is completely covered by the sleeve 32 over the entire circumference.

Therefore, since the emitted light emitted from the light source 20 is not emitted as it is to the outside through the sleeve opening H32, the light source device 1B is highly safe.

Third Modification of First Embodiment

Figure 10:
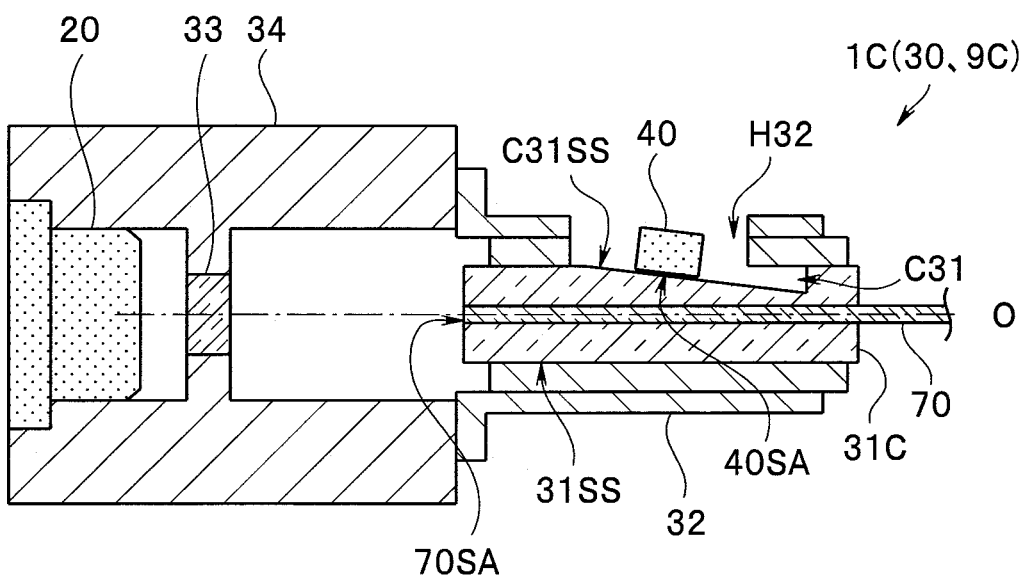
FIG. 10 is a cross-sectional view of a light source device including an optical connection module for an endoscope according to a third modification of the first embodiment.

As illustrated in FIG. 10, in the light source device 1C including the optical connection module according to the present modification, the planar region C31SS formed on the side surface 31SS of a ferrule 31C is tilted toward the ferrule end surface 31SA. That is, the light receiving surface 40SA of the optical sensor 40 is arranged in a state of facing the traveling direction of the emitted light guided inside the ferrule 31C.

More scattered light is incident on the optical sensor 40 in the light source device 1C than that in the light source device 1B. The light source device 1C can accurately detect the light quantity because the optical sensor 40 receives the scattered light having an appropriate light quantity. Accordingly, the light source device 1C can emit illumination light having an appropriate light quantity.

Note that in the light source devices 1 and 1A to 1C as well, a part of the emitted light condensed by the lens 33 may be directly incident on the ferrule end surface 31SA or reflected by the ferrule end surface 31SA. That is, the numerical aperture (NA) of the lens 33 may be greater than the numerical aperture (NA) of the optical fiber 70. However, in order to secure the light quantity of the illumination light, it is preferable that the numerical aperture (NA) of the lens 33 be equal to or less than the numerical aperture (NA) of the optical fiber 70.

Furthermore, in the light source devices 1, 1B, and 1C, as in the light source device 1A, the fiber end surface 70SA may be tilted relative to the surface perpendicular to the optical axis O of the optical fiber 70. The tilt angle of the fiber end surface 70SA is preferably an angle at which the emitted light reflected by the fiber end surface 70SA is not incident on the lens 33.

Note that it goes without saying that, when one light source device has all the respective configurations of the light source devices 1A to 1C, the one light source device has all the respective effects of the light source devices 1A to 1C. Furthermore, it goes without saying that the endoscopes 9A to 9C respectively having the light source devices 1A to 1C each have the effects of the endoscope 9, and further respectively have the effects of the light source devices 1A to 1C.

Second Embodiment

A light source system 8 for an endoscope according to a second embodiment (hereinafter, referred to as a "light source system 8") includes two light source devices 1X and 1Y. Since the light source devices 1X and 1Y have the same effects as those of the light source device 1 and the like, constituent elements having the same functions are given the same reference numerals, and the description thereof will be omitted.

Figure 11:
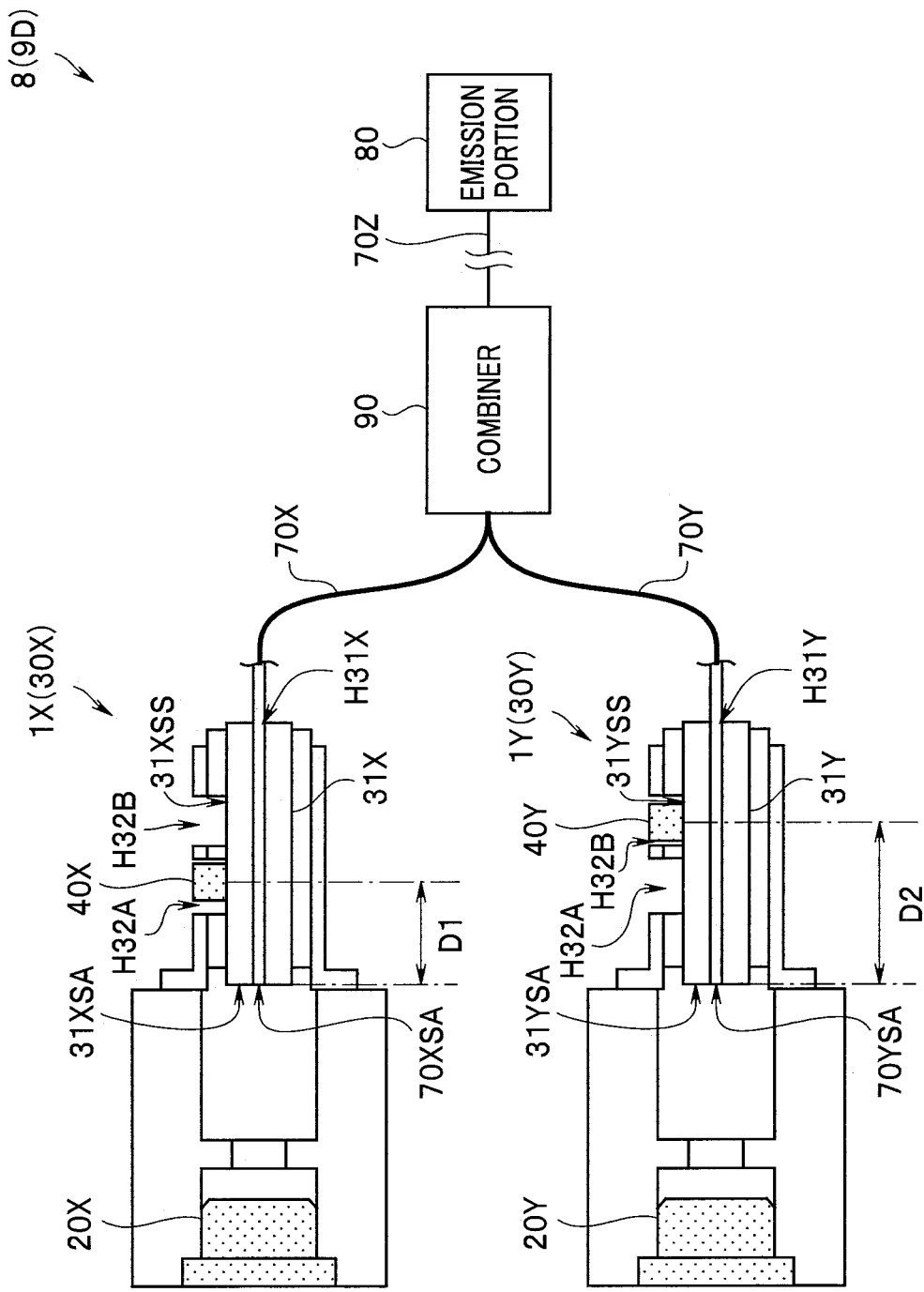
FIG. 11 is a configuration diagram of a light source system for an endoscope according to a second embodiment.

That is, as illustrated in FIG. 11, the light source system 8 has the first light source device 1X, the second light source device 1Y, a combiner 90, and a third optical fiber 70Z.

The first light source device 1X includes: a first optical fiber 70X having a first fiber end surface 70XSA and configured to guide a part of first emitted light emitted from a first light source 20X and incident on the first fiber end surface 70XSA; a first ferrule 31X having a first ferrule end surface 31XSA with an opening of a first through-hole H31X into which the first optical fiber 70X is inserted, including a scatterer configured to scatter, in an inside of the first ferrule 31X, another part of the first emitted light incident on the first ferrule end surface 31XSA, and configured to emit first scattered light generated by scattering from a first side surface 31XSS; and a first optical sensor 40X arranged in the periphery of the first side surface 31XSS and configured to receive the first scattered light.

The second light source device 1Y includes: a second optical fiber 70Y having a second fiber end surface 70YSA and configured to guide a part of second emitted light emitted from a second light source 20Y and incident on the second fiber end surface 70YSA; a second ferrule 31Y having a second ferrule end surface 31YSA with an opening of a second through-hole H31Y into which the second optical fiber 70Y is inserted, including a scatterer configured to scatter, in an inside of the second ferrule 31Y, another part of the second emitted light incident on the second ferrule end surface 31YSA, and configured to emit second scattered light generated by scattering from a second side surface 31YSS; and a second optical sensor 40Y arranged in the periphery of the second side surface 31YSS and configured to receive the second scattered light.

The combiner 90 multiplexes the first emitted light guided by the first optical fiber 70X and the second emitted light guided by the second optical fiber 70Y. The third optical fiber 70Z guides third light emitted from the combiner 90. The third light is at least one of the first emitted light and the second emitted light.

A first wavelength of the first emitted light is shorter than a second wavelength of the second emitted light. Furthermore, a distance D1 between the first optical sensor 40X and the first fiber end surface 70XSA is shorter than a distance D2 between the second optical sensor 40Y and the second fiber end surface 70YSA.

For example, the first light source 20X emits violet first emitted light having a wavelength of 405 nm, and the second light source 20Y emits blue second emitted light having a wavelength of 450 nm.

Note that the first light source device 1X and the second light source device 1Y differ from each other only in the light sources, and the other configurations are the same. Since many common members are included, the light source system 8 is easy to manufacture and reduce the cost.

The first optical sensor 40X and the second optical sensor 40Y are the same as typical PDs, and have wavelength-dependent light-receiving sensitivity. The light-receiving sensitivity for violet light having a shorter wavelength than blue light is lower than the light-receiving sensitivity for blue light.

On the other hand, the light quantity of the emitted light that is incident on each of the ferrule end surfaces 31XSA and 31YSA and is guided to the rear end surface 31SB while being scattered inside each of the ferrules 31X and 31Y reduces as the light is guided. In accordance therewith, the scattered light emitted from the side surface 31SS also decreases as the light is guided.

The light source system 8 is provided with two light source devices respectively having light sources of different wavelengths, and the optical sensors are respectively arranged at positions where the optimum light quantities for respective wavelengths are obtained. That is, the first optical sensor 40X is arranged in the first sleeve opening H32A, and the second optical sensor 40Y is arranged in the second sleeve opening H32B.

The light source system 8 can accurately detect the light quantities of the first wavelength light and the second wavelength light.

Figure 12:
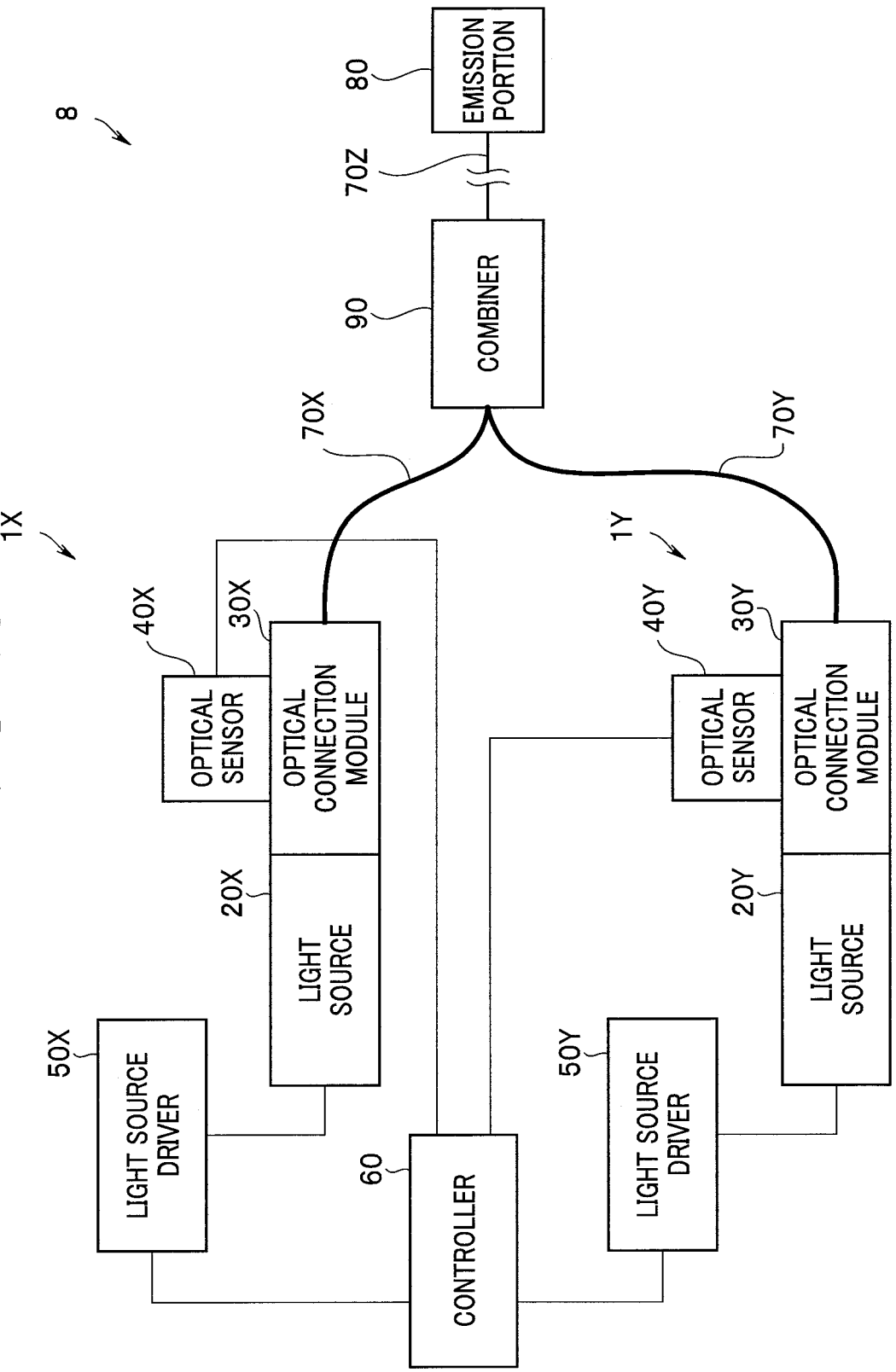
FIG. 12 is a configuration diagram of the light source system for the endoscope according to the second embodiment.

As illustrated in FIG. 12, the light source system 8 is further provided with the controller 60 that adjusts the light quantities of the first emitted light and the second emitted light by controlling the first light source 20X and the second light source 20Y in accordance with output values of the first optical sensor 40X and the second optical sensor 40Y.

For example, in the case where white light is emitted from the emission portion 80 as illumination light, a driving signal of the second light source 20Y is controlled, but the first light source 20X is not supplied with a driving signal.

Accordingly, the third optical fiber 70Z guides only blue light emitted from the second light source 20Y. The blue light causes the phosphor disposed in the emission portion 80 to generate yellow light. Accordingly, from the emission portion 80, white light including the blue light and the yellow light is emitted as illumination light.

On the other hand, in the case where narrow band violet light is emitted from the emission portion 80 as illumination light, the driving signal of the first light source 20X is controlled, but the second light source 20Y is not supplied with the driving signal.

The third optical fiber 70Z guides the violet light emitted from the first light source 20X. The violet light does not excite the phosphor disposed in the emission portion 80. From the emission portion 80, the violet light is emitted as illumination light.

The light source system 8 can accurately detect the light quantities because the two optical sensors each receive the scattered light having different wavelength by an appropriate light quantity. Accordingly, the light source system 8 can emit illumination light having an appropriate light quantity. An endoscope 9D having the light source system 8 can obtain an endoscope image with appropriate brightness by the illumination light having the appropriate light quantity. That is, the endoscope 9D can obtain the endoscope image with the appropriate brightness regardless of whether the illumination light is the white light or the violet light.

Note that the emitted light of each of the light source devices 1X and 1Y of the light source system 8 is not limited to the blue light or the violet light. Furthermore, the light source system 8 may be provided with three or more light source devices.

When the light source devices 1X and 1Y have the configurations of the light source devices 1A to 1C, it goes without saying that the light source system 8 and the endoscope 9D having the light source system 8 have the effects of the light source devices 1A to 1C.

Furthermore, in the above description, the light source device or the like that emits illumination light having a large light quantity, which particularly has a remarkable effect of the present invention, has been described. However, the same effects can be obtained even in a light source device or the like that outputs an optical signal having a relatively small light quantity.

The present invention is not limited to the embodiments, the modifications, and the like described above, and various changes, combinations, and applications can be made without departing from the gist of the invention.

What is claimed is:

1. An optical connection module for an endo scope comprising:
   an optical fiber having a fiber end surface and configured to guide a part of emitted light emitted from a light source and incident on the fiber end surface;
   a ferrule having a ferrule end surface with an opening of a through-hole into which the optical fiber is inserted, the ferrule including a scatterer configured to scatter, in an inside of the ferrule, a part of the emitted light incident on the ferrule end surface, the ferrule being configured to emit scattered light generated by scattering from a side surface; and
   an optical sensor arranged in a periphery of the side surface of the ferrule and configured to receive the scattered light;
   wherein the ferrule is configured such that a light quantity of the scattered light emitted from a rear end surface on an opposite side of the ferrule end surface is greater than 0.1% and less than 80% of a light quantity of the emitted light incident perpendicularly on the ferrule end surface.

2. The optical connection module for the endoscope according to claim 1, wherein the scatterer of the ferrule is formed of a mixed material of a plurality of materials having different refractive indexes or a polycrystalline material.

3. The optical connection module for the endoscope according to claim 1, further comprising:
   a lens configured to condense the emitted light on the fiber end surface; and
   a holder having an inner surface configuring a space including an optical path of the emitted light to be condensed by the lens, and to which the lens and the ferrule are fixed, wherein
   the emitted light reflected by the inner surface of the holder is incident on the ferrule end surface.

4. The optical connection module for the endoscope according to claim 3, wherein
   a numerical aperture of the lens is equal to or less than a numerical aperture of the optical fiber, and
   the emitted light reflected by the fiber end surface is further reflected by the inner surface and is incident on the ferrule end surface.

5. The optical connection module for the endoscope according to claim 3, wherein the inner surface of the holder has a tilted surface tilted toward the ferrule end surface, and the emitted light reflected by the fiber end surface and the tilted surface is incident on the ferrule end surface.

6. The optical connection module for the endoscope according to claim 1, wherein the fiber end surface is perpendicular to an optical axis of the optical fiber.

7. The optical connection module for the endoscope according to claim 1, wherein the fiber end surface is tilted relative to an optical axis of the optical fiber.

8. The optical connection module for the endoscope according to claim 1, wherein
   a cutout region is formed on the side surface of the ferrule, and
   the optical sensor is arranged in the cutout region.

9. The optical connection module for the endoscope according to claim 1, wherein
   the cutout region is a plane, and
   the plane is tilted toward the ferrule end surface.

10. The optical connection module for the endoscope according to claim 1, further comprising:
    a sleeve configured to hold the ferrule by covering the side surface of the ferrule, wherein
    the sleeve has one or more sleeve openings, and the optical sensor is installed in one of the one or more sleeve openings.

11. The optical connection module for the endoscope according to claim 10, wherein a plurality of optical sensors are installed in the one or more sleeve openings in a direction parallel to the optical axis of the optical fiber.

12. The optical connection module for the endoscope according to claim 10, wherein the one or more sleeve openings comprise a plurality of sleeve openings in the direction parallel to the optical axis of the optical fiber, and the optical sensor is installed in at least one of the plurality of sleeve openings.

13. The optical connection module for the endoscope according to claim 10, wherein
    a cutout region is formed on the side surface of the ferrule, and the optical sensor is arranged in the cutout region,
    the cutout region is not formed up to the ferrule end surface, and
    a region of the side surface of the ferrule, which is closer to the light source than the cutout region, is covered by the sleeve.

14. The optical connection module for the endoscope according to claim 1, wherein the emitted light is illumination light.

15. An endoscope comprising:
    an optical connection module comprising:
       an optical fiber having a fiber end surface and configured to guide a part of emitted light emitted from a light source and incident on the fiber end surface;
       a ferrule having a ferrule end surface with an opening of a through-hole into which the optical fiber is inserted, the ferrule including a scatterer configured to scatter, in an inside of the ferrule, a part of the emitted light incident on the ferrule end surface, the ferrule being configured to emit scattered light generated by scattering from a side surface; and
       an optical sensor arranged in a periphery of the side surface of the ferrule and configured to receive the scattered light;
       wherein the ferrule is configured such that a light quantity of the scattered light emitted from a rear end surface on an opposite side of the ferrule end surface is greater than 0.1% and less than 80% of a light quantity of the emitted light incident perpendicularly on the ferrule end surface.

16. An endoscope system comprising:
    a light source device including an optical connection module, and
    an endoscope configured to emit illumination light guided by the light source device,
    wherein the optical connection module comprising:
       an optical fiber having a fiber end surface and configured to guide a part of emitted light emitted from a light source and incident on the fiber end surface;
       a ferrule having a ferrule end surface with an opening of a through-hole into which the optical fiber is inserted, the ferrule including a scatterer configured to scatter, in an inside of the ferrule, a part of the emitted light incident on the ferrule end surface, the ferrule being configured to emit scattered light generated by scattering from a side surface; and an optical sensor arranged in a periphery of the side surface of the ferrule and configured to receive the scattered light;

wherein the ferrule is configured such that a light quantity of the scattered light emitted from a rear end surface on an opposite side of the ferrule end surface is greater than 0.1% and less than 80% of a light quantity of the emitted light incident perpendicularly on the ferrule end surface.

* * * * *